United States Patent [19]

Bronn

[11] Patent Number: 4,555,573
[45] Date of Patent: Nov. 26, 1985

[54] CERTAIN 6-BENZAMIDOMETHYL-2(1H)-PYRIDONE DERIVATIVES

[75] Inventor: William R. Bronn, Maplewood, Minn.

[73] Assignee: Riker Laboratories, Inc., St. Paul, Minn.

[21] Appl. No.: 551,967

[22] Filed: Nov. 15, 1983

[51] Int. Cl.$^4$ ........................................... C07D 213/56
[52] U.S. Cl. .................................. 546/291; 546/233; 546/300
[58] Field of Search ........................................ 546/291

[56] References Cited

U.S. PATENT DOCUMENTS

| | | | |
|---|---|---|---|
| 3,655,728 | 4/1972 | Mendel | 560/56 |
| 3,719,687 | 3/1973 | Mendel et al. | 548/567 |
| 3,900,481 | 8/1975 | Banitt et al. | 546/224 |
| 4,071,524 | 1/1978 | Banitt | 546/231 |
| 4,097,481 | 6/1978 | Banitt et al. | 546/234 |
| 4,339,587 | 7/1982 | Banitt | 546/337 |

OTHER PUBLICATIONS

Journal of Medicinal Chemistry, 20, 821 (1977).

Primary Examiner—Alan L. Rotman
Attorney, Agent, or Firm—Donald M. Sell; James A. Smith; Robert W. Sprague

[57] ABSTRACT

Certain substituted pyridine compounds are useful synthetic intermediates for preparing compounds of pharmaceutical interest. A synthetic process for using these intermediates is also described.

3 Claims, No Drawings

CERTAIN 6-BENZAMIDOMETHYL-2(1H)-PYRIDONE DERIVATIVES

TECHNICAL FIELD

This invention relates to substituted pyridine compounds and a synthetic process which are useful in the preparation of compounds of pharmaceutical interest.

BACKGROUND OF THE INVENTION

Esters of benzoic acid which are substituted on the aromatic ring by 1,1-dihydroperfluoroalkoxy substituents and exhibit anesthetic activity are described in U.S. Pat. No. 3,655,728. Amides of benzoic acid which are substituted on the aromatic ring by 1,1-dihydroperfluoroalkoxy substituents and exhibit antiarrhythmic activity are described in U.S. Pat. No. 3,719,687. U.S. Pat. Nos. 3,900,481, 4,071,524 and 4,097,481 describe antiarrhythmic agents including, inter alia, N-(piperidylmethyl)benzamides substituted by one or more 1,1-dihydroperfluoroalkoxy groups. Above-mentioned U.S. Pat. No. 3,900,481 discloses the compound 2,5-bis(2,2,2-trifluoroethoxy)-N-(2-piperidylmethyl)-benzamide, a particularly useful antiarrhythmic agent also known as flecainide. An article appearing in the Journal of Medicinal Chemistry, Vol. 20, pg. 821 (1977), discloses many of the compounds of the patents, and also discloses various additional compounds such as 2-(2,2,2-trifluoroethoxy)-N-(2-piperidylmethyl)benzamides in which the aromatic ring is substituted in the 5-position by a non-functional group, i.e., methyl, chloro or fluoro.

U.S. Pat. No. 4,339,587 discloses 5-hydroxy-2-(2,2,2-trifluoroethoxy)-N-(2-piperidylmethyl)benzamide and synthetic intermediates useful in the synthesis thereof. This compound is a metabolite of flecainide, and is useful as an intermediate in the synthesis of flecainide and as an antiarrhythmic agent itself.

DETAILED DESCRIPTION OF THE INVENTION

In one aspect, the present invention relates to compounds of Formula I

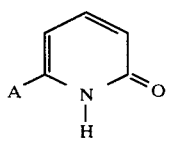

wherein A is selected from the group consisting of

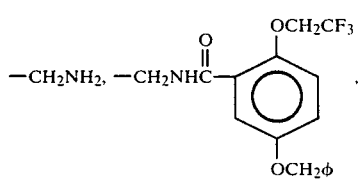

-continued

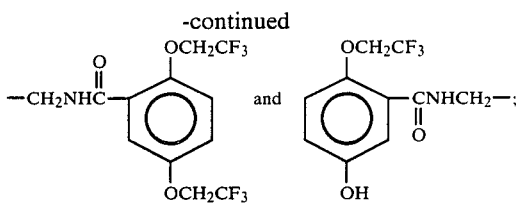

and acid addition salts thereof when A is —CH$_2$NH$_2$.

In another aspect, the present invention relates to compounds of Formula II

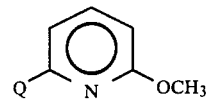

wherein Q is selected from the group consisting of —CH$_2$NH$_2$ and

and acid addition salts thereof when Q is —CH$_2$NH$_2$.

The compounds of Formulas I and II are useful as synthetic intermediates in the preparation of 5-hydroxy-N-(6-oxo-2-piperidylmethyl)-2-(2,2,2-trifluoroethoxy)-benzamide (a metabolite of flecainide) and 2,5-bis(2,2,2-trifluoroethoxy)-N-(6-oxo-2-piperidylmethyl)benzamide.

In still another aspect, the present invention relates to a process for preparing 5-hydroxy-N-(6-oxo-2-piperidylmethyl)-2-(2,2,2-trifluoroethoxy)benzamide and 2,5-bis(2,2,2-trifluoroethoxy)-N-(6-oxo-2-piperidylmethyl)benzamide using the above intermediates.

Synthetic 5-hydroxy-N-(6-oxo-2-piperidylmethyl)-2-(2,2,2-trifluoroethoxy)benzamide is useful as a standard for monitoring the metabolism of flecainide in mammals. As for 2,5-bis(2,2,2-trifluoroethoxy)-N-(6-oxo-2-piperidylmethyl)benzamide, it is believed that this compound could be reduced to provide flecainide and that it therefore is a useful synthetic intermediate.

Acid-addition salts of certain of the compounds of Formulas I and II may be prepared by conventional techniques. Typically, such salts are prepared by reacting the respective compound with an equimolar amount of a relatively strong acid, preferably an inorganic acid such as hydrochloric, sulfuric or phosphoric acid in a polar solvent. Isolation of the salt is facilitated by the addition of a solvent in which the salt is insoluble, an example of such a solvent being diethyl ether. Formation of an acid-addition salt may be desirable during purification of the respective compounds.

The following reaction scheme shows the synthetic route by which the compounds of Formulas I and II may be obtained and the manner in which they may be used. In the reaction scheme, B is —CH$_2\phi$ or —CH$_2$CF$_3$; and Y is —CH$_2$CF$_3$ or hydrogen, with the provisos that Y is —CH$_2$CF$_3$ when B is —CH$_2$CF$_3$, and Y is hydrogen when B is —CH$_2\phi$.

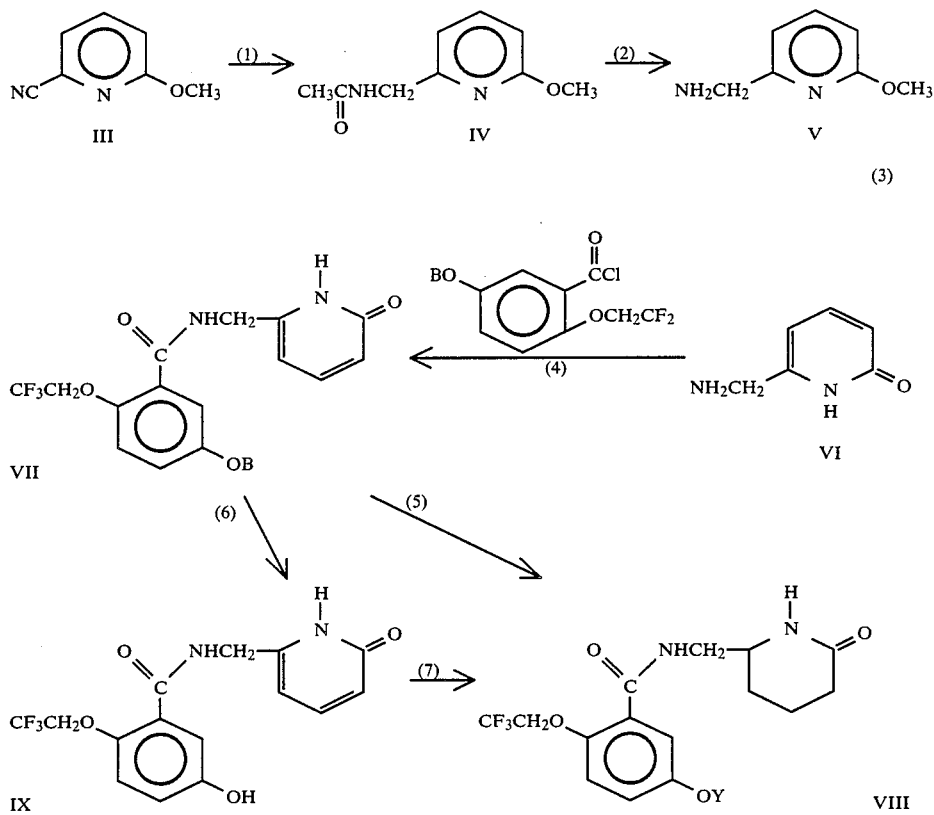

In step (1) the known compound 2-cyano-6-methoxypyridine (Formula III) is reductively acetylated to provide the novel 2-acetamidomethyl-6-methoxypyridine (Formula IV). The reductive acetylation is carried out catalytically in the presence of hydrogen gas and Raney nickel catalyst. An acetate salt such as sodium acetate is required, preferably in 0.1 to 1.0 molar amounts relative to the compound of Formula III. A large excess of acetic anhydride is used. The reaction occurs readily at moderate (0° to 50° C.) temperatures.

The compound of Formula IV is deacetylated by conventional acid hydrolysis techniques in step (2) to provide novel 2-aminomethyl-6-methoxypyridine (Formula V). It has been found that dilute aqueous hydrochloric acid accomplishes this reaction readily with simple refluxing. The compound is obtained as a hydrochloride addition salt.

In step (3) the 2-aminomethyl-6-methoxypyridine of Formula V is converted to novel 6-aminomethyl-2(1H)-pyridone (Formula VI). This conversion is somewhat slower than the deacetylation of step (2), but it occurs readily also. Indeed, the reaction conditions of step (2), if carried out for several hours, were found to partially achieve the reaction of step (3). Step (3) was completed by heating and refluxing compound of Formula V (or a mixture of IV and V) in 48% hydrobromic acid. The product is obtained as a hydrobromide addition salt.

Step (4) involves the reaction of 6-aminomethyl-2(1H)-pyridone (Formula VI) with 5-benzyloxy-2-(2,2,2-trifluoroethoxy)benzoyl chloride, (Formula VIA), a compound described in U.S. Pat. No. 4,339,587. This reaction can also be carried out between 6-aminomethyl-2(1H)-pyridone and the known compound, 2,5-bis(2,2,2-trifluoroethoxy)benzoyl chloride. This reaction may be carried out in an inert solvent such as acetone with (preferably) or without an acid acceptor such as sodium carbonate.

Compounds of Formula VII wherein B is 2,2,2-trifluoroethyl can be converted directly by catalytic reduction to a novel compound of Formula VIII wherein Y is trifluoroethyl. This reduction is rapidly accomplished as shown in step (5) on a Parr apparatus at about 20° C. using rhodium on alumina ($Al_2O_3$) as catalyst in the presence of hydrogen gas. It is preferred to use a non-reactive solvent such as a lower alkanol, for example, ethanol and/or methanol.

The compound of Formula VII wherein B is benzyl is converted as shown in step (6) to a novel compound of Formula IX by catalytic reduction on a Parr apparatus at about 20° C. The catalyst used is palladium on charcoal. The reduction is carried out in an inert solvent such as a lower alkanol, for example, ethanol and/or methanol.

In step (7), the compound of Formula IX is reduced to provide a compound of Formula VIII wherein Y is hydrogen. This reduction is readily accomplished as shown in the presence of hydrogen gas using rhodium on alumina as catalyst. The reduction occurs rapidly at 20° C. in a nonreactive solvent such as a lower alkanol, for example, ethanol and/or methanol.

The following examples illustrate the preparation of compounds of the invention.

EXAMPLE 1

Preparation of 2-Acetamidomethyl-6-methoxypyridine

A mixture of 1.0 g (7.46 mmole) of 2-cyano-6-methoxypyridine, 0.37 g (4.48 mmole) of sodium acetate, 25 ml of acetic anhydride and about 1.0 g of Raney nickel was hydrogenated on a Parr apparatus for about 5.5 hours. The mixture was filtered, and then evaporated with warming in vacuo to provide 2-acetamidomethyl-6-methoxypyridine. The structural assignment was supported by infrared spectral analysis.

EXAMPLE 2
Preparation of 2-Aminomethyl-6-methoxypyridine

The crude product, 2-acetamidomethyl-6-methoxypyridine from Example 1, was combined with 10 ml of 6N hydrochloric acid, and the resulting mixture was heated at its reflux temperature for about 16 hours. The mixture was evaporated to provide a tan solid residue. The product was determined by infrared and nuclear magnetic resonance spectral analyses to be a mixture of 2-aminomethyl-6-methoxypyridine hydrochloride and 6-aminomethyl-2(1H)-pyridone hydrochloride.

EXAMPLE 3
Preparation of 6-Aminomethyl-2(1H)-pyridone

The crude product from Example 2 was combined with 10 ml of 48% hydrobromic acid, and the resulting mixture was heated at its reflux temperature for one hour. Evaporation to dryness provided 6-aminomethyl-2(1H)-pyridone hydrobromide as a water-soluble solid. The structural assignment was supported by infrared and nuclear magnetic resonance spectral analyses.

EXAMPLE 4
Preparation of 6-[5-Benzyloxy-2-(2,2,2-trifluoroethoxy)benzamidomethyl]-2(1H)-pyridone To a stirred mixture of the crude product from Example 3, 20 ml of acetone and 4.7 g of sodium carbonate was added dropwise 2.8 g (8.21 mmole) of 5-benzyloxy-2-(2,2,2-trifluoroethoxy)benzoyl chloride in 10 ml of acetone. The mixture was stirred at about 20° C. for about 16 hours. To the mixture was added 50 ml of acetone, and the resulting inorganic residue was separated by filtration and washed with acetone. The filtrate and washings were combined and evaporated. This residue was dissolved in benzene, and the solution was washed sequentially with 10% aqueous sodium carbonate solution, 2% acetic acid, water, saturated aqueous sodium bicarbonate solution and saturated aqueous sodium chloride solution. The organic solution was dried over magnesium sulfate, and then filtered and evaporated. The residue was boiled in carbon tetrachloride, and the mixture was cooled and the solid was separated by filtration. The solid was purified by chromatography on 30 g of silica gel. The column was eluted sequentially with 5% ethyl acetate in dichloromethane and 2% methanol in dichloromethane. The product was obtained as a white solid, 6-[5-benzyloxy-2-(2,2,2-trifluoroethoxy)benzamidomethyl]-2(1H)-pyridone. The structural assignment was supported by infrared and nuclear magnetic resonance spectral analyses.

EXAMPLE 5
Preparation of 6-[5-Hydroxy-2-(2,2,2-trifluoroethoxy)benzamidomethyl]-2(1H)-pyridone A mixture of 0.5 g of 6-[5-benzyloxy-2-(2,2,2-trifluoroethoxy)benzamidomethyl]-2(1H)-pyridone, 60 ml of ethanol, 40 ml of methanol and 0.043 g of 10% palladium on charcoal was hydrogenated on a Parr apparatus at about 20° C. for about 16 hours. Filtration followed by evaporation of the filtrate provided a residue which was triturated with acetonitrile. The solid was separated by filtration and washed with acetonitrile to provide 6-[5-hydroxy-2-(2,2,2-trifluoroethoxy)benzamidomethyl]-2(1H)-pyridone. The structural assignment was supported by infrared and nuclear magnetic resonance spectral analyses.

EXAMPLE 6
Preparation of 5-Hydroxy-N-(6-oxo-2-piperidylmethyl)-2-(2,2,2-trifluoroethoxy)benzamide A mixture of 0.16 g (0.468 mmole) of 6-[5-hydroxy-2-(2,2,2-trifluoroethoxy)benzamidomethyl]-2(1H)-pyridone, 0.05 g of 5% rhodium on alumina and 50 ml of methanol was hydrogenated on a Parr apparatus for 50 minutes. The mixture was filtered, the filtrate was evaporated, and the residue was dried to provide 5-hydroxy-N-(6-oxo-2-piperidylmethyl)-2-(2,2,2-trifluoroethoxy)benzamide. The structural assignment was confirmed by comparison of infrared and nuclear magnetic resonance spectra to those of the same compound prepared by an alternative synthetic procedure.

What is claimed is:

1. A compound of the formula

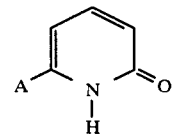

wherein A is selected from the group consisting of

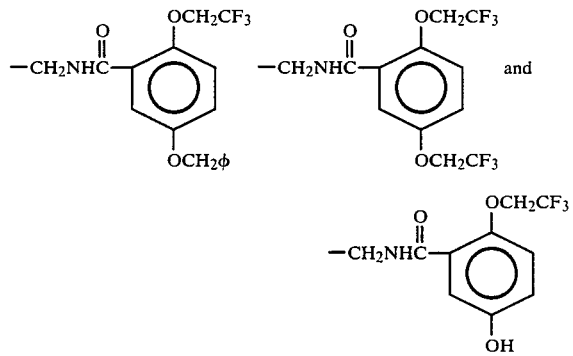

2. A compound of claim 1 wherein A is

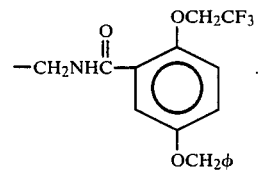

3. A compound of claim 1 wherein A is

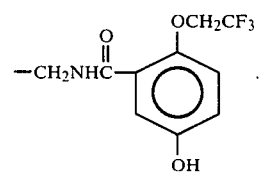

* * * * *